United States Patent
Chuang et al.

(10) Patent No.: US 9,897,567 B2
(45) Date of Patent: Feb. 20, 2018

(54) DETECTION METHOD FOR DETECTING BLOOD GLUCOSE AND HEMOGLOBIN OF BLOOD SAMPLE

(71) Applicant: DELBio, INC., Taoyuan (TW)

(72) Inventors: Ya-Hsin Chuang, Taoyuan (TW);
Chih-Wei Weng, Taoyuan (TW);
Tsung-Hsuan Tsai, Taoyuan (TW);
Chih-Cheng Yang, Taoyuan (TW);
Yi-An Chou, Taoyuan (TW)

(73) Assignee: Delbio, Inc., Taoyuan (TW)

(*) Notice: Subject to any disclaimer, the term of this patent is extended or adjusted under 35 U.S.C. 154(b) by 67 days.

(21) Appl. No.: 15/205,465

(22) Filed: Jul. 8, 2016

(65) Prior Publication Data
US 2016/0320331 A1 Nov. 3, 2016

Related U.S. Application Data

(63) Continuation-in-part of application No. 14/591,503, filed on Jan. 7, 2015.

(51) Int. Cl.
*G01N 27/327* (2006.01)

(52) U.S. Cl.
CPC ..... *G01N 27/3274* (2013.01); *G01N 27/3272* (2013.01); *G01N 27/3273* (2013.01)

(58) Field of Classification Search
CPC .................................. G01N 27/327–27/3274
USPC .................... 204/403.01–403.15; 205/792
See application file for complete search history.

(56) References Cited

U.S. PATENT DOCUMENTS

| | | | |
|---|---|---|---|
| 6,916,410 B2 | 7/2005 | Katsuki | |
| 6,982,027 B2 | 1/2006 | Yagi | |
| 7,135,100 B1 | 11/2006 | Lau | |
| 2007/0062822 A1 | 3/2007 | Fujiwara | |
| 2007/0131549 A1 | 6/2007 | Cai | |
| 2007/0131565 A1* | 6/2007 | Fujiwara | C12Q 1/001 205/777.5 |

(Continued)

FOREIGN PATENT DOCUMENTS

| | | |
|---|---|---|
| CN | 101308134 A | 11/2008 |
| TW | 201350840 A | 12/2013 |

OTHER PUBLICATIONS

Entry entitled "Linearizing Data" at the A Den of Inquiry, website <http://www.denofinquiry.com/resources/misc/linearizing.php>, published Sep. 12, 2006, downloaded Feb. 18, 2016.

*Primary Examiner* — Bach T Dinh
(74) *Attorney, Agent, or Firm* — Muncy, Geissler, Olds & Lowe, P.C.

(57) ABSTRACT

A detection method for detecting blood glucose value and blood hemoglobin value includes the steps: applying a first voltage to a blood sample and obtaining a first blood glucose value; applying a second voltage to the blood sample and obtaining a second blood glucose value; applying a third voltage to the blood sample and obtaining a hematocrit index and a hemoglobin index; transforming the hematocrit index into a hematocrit value and calibrating the second blood glucose value according to the hematocrit value; and transforming the hemoglobin index into a hemoglobin value. The detection method is advantageous for simultaneously detecting the blood glucose and hemoglobin by a single meter with a single strip.

13 Claims, 6 Drawing Sheets

(56) References Cited

U.S. PATENT DOCUMENTS

2012/0080326 A1* 4/2012 Chatelier ............... C12Q 1/001
                                                        205/782
2013/0062221 A1* 3/2013 Cai .................... G01N 27/3277
                                                        205/780.5
2013/0334064 A1   12/2013 Nien et al.

* cited by examiner

DETECTION METHOD FOR DETECTING BLOOD GLUCOSE AND HEMOGLOBIN OF BLOOD SAMPLE

CROSS REFERENCE TO RELATED APPLICATIONS

This application is a continuation-in-part patent (CIP) application of U.S. Ser. No. 14/591,503, filed on Jan. 7, 2015, which claims priority under 35 U.S.C. § 119(a) on Patent Application No(s). 103121860, filed in Taiwan, Republic of China on Jun. 25, 2014, the entire contents of which are hereby incorporated by reference.

BACKGROUND OF THE INVENTION

Field of Invention

The present invention relates to a detection method for simultaneously detecting blood glucose and whole blood hemoglobin of blood sample.

Related Art

With the progress of technology and changes of the human habits, the home health care gets more and more attention. The home health care is not only able to monitor the real-time status of patients, but capable of bringing many inspection items from hospital to patients' home.

Diabetes patients are one of the most common patients to be taken care at home. Generally, in order to effectively control and treat diabetes diseases patients, it is an important step to detect and monitor the blood glucose value of the patients. Besides, over 40% of diabetes patients also have renal dysfunction or renal failure, so it is necessary to monitor the kidney function of the patients earlier before the symptom of renal dysfunction or failure. Once the kidney function is abnormal, the creation of hemoglobin will be sufficiently decreased so as to reduce the hematopoietic function and reduce the amount of hemoglobin. In practice, the detected value of hemoglobin can be a critical index for monitoring the kidney function. According to the above detections, to effectively monitor the diabetes and accompanying renal dysfunction or renal failure in real-time.

Regarding the detection of blood glucose, the home-use or portable blood glucose meters used recently exist greater error value which is usually criticized by most users, and the most influential factors includes the hematocrit (HCT) of blood samples. The effects caused by the difference between hematocrit includes the difference between the stiffness of blood and the differences between the serum volume; the former factor causes further difference of electron transfer efficiency, and the latter factor causes the difference of testing standard. Hence, many kinds of methods used for testing hematocrit of the blood sample are developed in recent years.

The methods recently used for testing the hematocrit include flow velocity method, spectroscopic method, filtration membrane method, and especially the electrochemical method. The electrochemical method uses electrochemical sensor strip to test most substances in the testing solution, and then, compensating the blood glucose with the measured numerical value to make the testing result more close to the real situation of the patients.

However, the electrochemical method still remains some limitation; for example, it needs to use direct current and alternating current alternatively. In addition, the conventional strip structure is too complicated to simplify the manufacturing procedure and to decrease the manufacturing time. Otherwise, the accuracy of the self-testing result by patients is still not enough because of the error of the hematocrit. The accuracy of the blood glucose compensation is also affected by the concentrations of the glucose or interferences in blood samples.

Though, the electrochemical method still has considerable advantages for testing blood glucose and hematocrit, and is placed great hopes for long time. Thus, the electrochemical method might have greater applications while the above problems are overcome. Briefly speaking, the electrochemical method still needs to be improved, especially for the aspect of the testing of the hematocrit and blood glucose compensating. This might have a great influence to the future self-testing blood glucose techniques. In addition, if the detections of blood glucose and hemoglobin can be done with a single procedure in a short time based on the advanced electrochemical technology, the detection time can be sufficiently reduced thereby making the patient a more comfortable detection experience.

Therefore, it is an important subject to provide a detection method for simultaneously detecting blood glucose and whole blood hemoglobin of blood sample by a dual-functional testing strip, which is able to remove the effect on glucose or interferences by the blood glucose value and hematocrit, and to obtain hemoglobin value.

SUMMARY OF THE INVENTION

In view of the foregoing, an objective of the invention is to provide a detection method for simultaneously detecting blood glucose and whole blood hemoglobin of blood sample by a dual-functional testing strip, which is able to remove the effect on glucose or interferences by the blood glucose value and hematocrit, and to obtain hemoglobin value.

To achieve the above objective, the present invention discloses a detection method for detecting a blood glucose value and a blood hemoglobin value of a blood sample. The detection method includes the steps of: applying a first voltage to the blood sample and obtaining a first blood glucose value; applying a second voltage to the blood sample and obtaining a second blood glucose value; applying a third voltage to the blood sample and obtaining a hematocrit index and a hemoglobin index; transforming the hematocrit index into a hematocrit value and calibrating the second blood glucose value according to the hematocrit value; and transforming the hemoglobin index into the blood hemoglobin value. The present invention is advantageous for simultaneously detecting the blood glucose and hemoglobin by a single meter with a single strip.

In one embodiment, the third voltage is between 1 and 4 volts.

In one embodiment, the third voltage is applied for 2 seconds.

In one embodiment, the step of obtaining the hematocrit index comprises obtaining a first median A1 of current values as the third voltage is applied from 0 to 0.5 seconds; and obtaining a second median A2 of current values as the third voltage is applied from 1 to 2 seconds. Herein, the hematocrit index is $(A1/A2) \times 100$.

In one embodiment, the step of obtaining the hemoglobin index comprises obtaining a third median B of current values as the third voltage is applied from 0 to 2 seconds. Herein, the hemoglobin index is $\ln[(A1/A2) \times (B/A2) \times 1000]$.

In one embodiment, the first, second and third voltages are direct voltages.

In one embodiment, the step of transforming the hematocrit index into the hematocrit value is performed based on a linear correlation formula.

To achieve the above objective, the present invention also discloses a detection method for detecting a blood glucose value and a blood hemoglobin value of a blood sample. The detection method includes the following steps of: applying a first voltage to the blood sample and obtaining a first blood glucose value; applying a second voltage to the blood sample and obtaining a second blood glucose value; applying a third voltage to the blood sample and obtaining a hematocrit index; transforming the hematocrit index into a hematocrit value and calibrating the second blood glucose value according to the hematocrit value; and obtaining the blood hemoglobin value according to the hematocrit value.

In one embodiment, the third voltage is between 1 and 4 volts.

In one embodiment, the third voltage is applied for 2 seconds.

In one embodiment, the step of obtaining the hematocrit index comprises obtaining a first median A1 of current values as the third voltage is applied from 0 to 0.5 seconds; and obtaining a second median A2 of current values as the third voltage is applied from 1 to 2 seconds. Herein, the hematocrit index is $(A1/A2) \times 100$.

In one embodiment, the first, second and third voltages are direct voltages.

In one embodiment, the step of transforming the hematocrit index into the hematocrit value is performed based on a linear correlation formula.

As mentioned above, the detection method of the invention is applied to detect the blood glucose and hemoglobin of a blood sample. In the detection procedure, the blood sample is injected into an electrochemical test strip, which is configured with a working electrode and an auxiliary electrode for conducting the electrochemical reaction of the blood sample. The present invention obtains a sensing current corresponding to the original blood glucose value, a sensing current for an optimum blood glucose value with removing the effect of interferences, and a hematocrit index (HCT index) corresponding to the blood sample by applying three-stage voltages in the specific range to the blood sample, and further calibrates the original blood glucose value according to the hematocrit index. Moreover, the present invention also transforms the hemoglobin index to obtain a blood hemoglobin value. In another embodiment of the invention, the present invention can also obtain the hematocrit value and the blood hemoglobin value according to the hematocrit index.

Compared with the conventional techniques, the detection method of the invention is to apply a first voltage and a second voltage to the blood sample for obtaining a first blood glucose value and a second blood glucose value, respectively. Since the second voltage is a reversed voltage with respect to the first voltage, it can effectively remove the effect of the interferences in the blood sample to the detected blood glucose value. Besides, the detection method is further to apply a third voltage, after applying the second voltage, to obtain a hematocrit index and a hemoglobin index of the blood sample. The obtained indexes can be processed to calibrate the blood glucose value and generate the blood hemoglobin value. In other words, the detection method of the invention can simultaneously retrieve accurate blood glucose value and blood hemoglobin value by a single strip in cooperated with a single measuring device within a single testing procedure. This feature can sufficiently reduce the detection time and simplify the detection processes.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

Figure 1A:
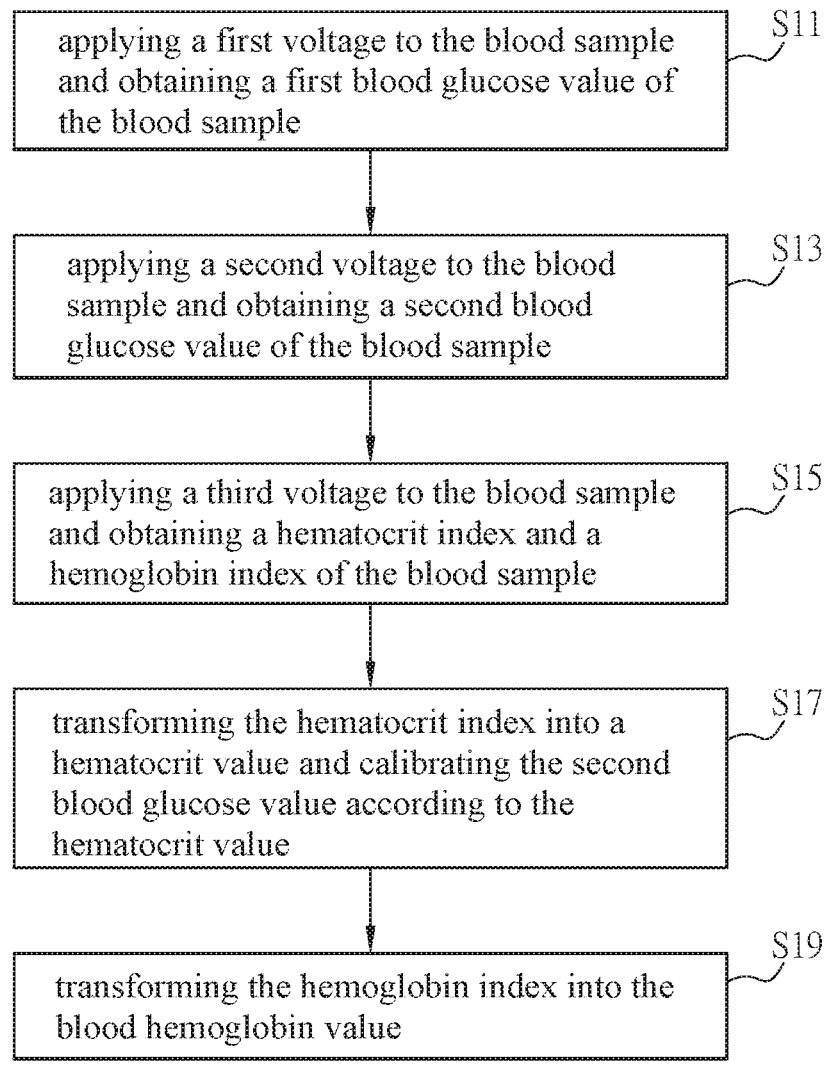
FIG. 1A is a flow chart of a detection method according to a preferred embodiment of the invention.

FIG. 1A is a flow chart of a detection method according to a preferred embodiment of the invention. With reference to FIG. 1A, the detection method includes at least the following steps of: applying a first voltage to the blood sample and obtaining a first blood glucose value of the blood sample (S11); applying a second voltage to the blood sample and obtaining a second blood glucose value of the blood sample (S13); applying a third voltage to the blood sample and obtaining a hematocrit index and a hemoglobin index of the blood sample (S15); transforming the hematocrit index into a hematocrit value and calibrating the second blood glucose value according to the hematocrit value (S17); and transforming the hemoglobin index into the blood hemoglobin value (S19).

To more explicitly illustrate the details of the methods of the present invention, the following takes an apparatus and a whole blood sample as the solution sample for example, and firstly illustrating the composition and the structure of the apparatus. Then, the method of the present invention will be specifically demonstrated based on the apparatus. However, the following description is for explicitly explanation, and is not meant to be construed in a limiting sense.

Figure 1B:
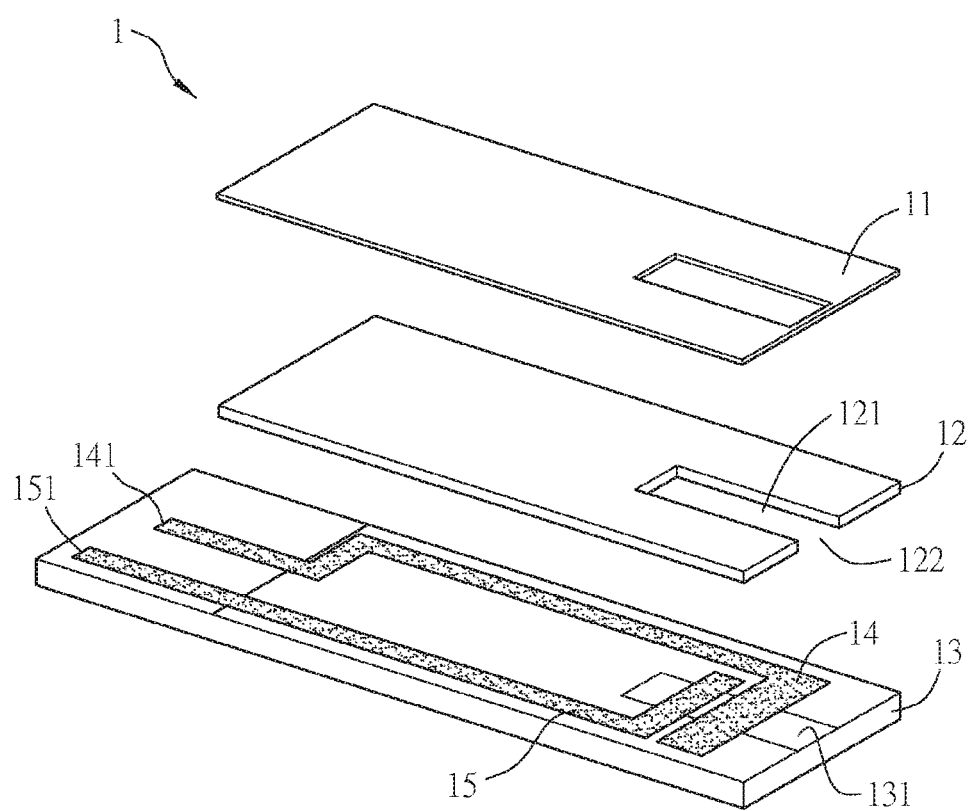
FIG. 1B is an exploded view of a testing strip applying the detection method of FIG. 1A.

FIG. 1B is an exploded view of a testing strip applying the detection method of FIG. 1A. As shown in FIG. 1B, the testing strip 1 includes a top layer 11, a middle layer 12, two electrodes and a base layer 13 in an order from top to bottom. However, the structure of the testing strip 1 mentioned above is not for limitation. The order and the relative correlation can be altered, or even adding other elements in the structure.

The base layer 13 is an electrically insulated substrate including but not limited for polyvinyl chloride, polystyrene, polyester, polycarbona, polywther, polyethene, polypropylene, polyethylene terephthalate, silica, or aluminum oxide. The two electrodes are working electrode 14 and auxiliary electrode 15. In this embodiment, the electrode structure is formed on the base layer 13 or other suitable places by screen printing in order to form the required shape. The working electrode 14 and the auxiliary electrode 15 are not limited to carbon, single metal, alloy, or other conductive material. Otherwise, the relative positions, the shapes, and the sizes of the working electrode 14 and the auxiliary electrode 15 are not meant to be construed in a limiting sense.

With reference to FIG. 1B, one end of the base layer 13 has a cathode 141 and an anode 151 formed by the working electrode 14 and the auxiliary electrode, respectively. Likewise, the relative correlation of the cathode 141 and the anode 151 are formed according to connection of the electrochemical cells and the direction electrons flow, and are not limited.

The other end of the base layer 13 has a reaction portion 131. The two electrodes 14, 15 are at least partially disposed and covering the reaction portion 131. In detail, by disposing the middle layer 12 which containing an inlet portion 121 relative to the reaction portion 131 on the base layer 13, the combination of the middle layer 12 and the base layer 13 is able to define a space for accommodating blood sample by the inlet portion 121, the thickness of the middle layer 12 thereof and the base layer 13. Thus, when blood sample is injected from the inlet portion 121 of the middle layer 12 into the reaction portion 131 through the inlet 122 (the space), the working electrode 14 and the auxiliary electrode 15 are able to contact the blood sample, and then further conduct the electrochemical reaction. The electrochemical reaction technique is well-understood by the person having ordinary skill in the art, and is not repeated here.

The detailed content related to the present invention of the electrochemical reaction technique mentioned above roughly includes fixing a reagent on the reaction portion 131 and making it react with a substance in a solution to be detected to generate an electrical signal. In this embodiment, the reagent used in the present invention is at least including an electron transfer substance. The electron transfer substance mentioned here includes tetrathiafulvalene, tetracyanoquinodimethan, meldola blue, Potassium ferrocyanide, ferrocene, or ferrocenedicarboxylic acid, and is not for limitation. Otherwise, the reagent used in the present invention also includes enzyme able to react with the substance to be tested, polymers, or stabilizer.

Figure 1C:
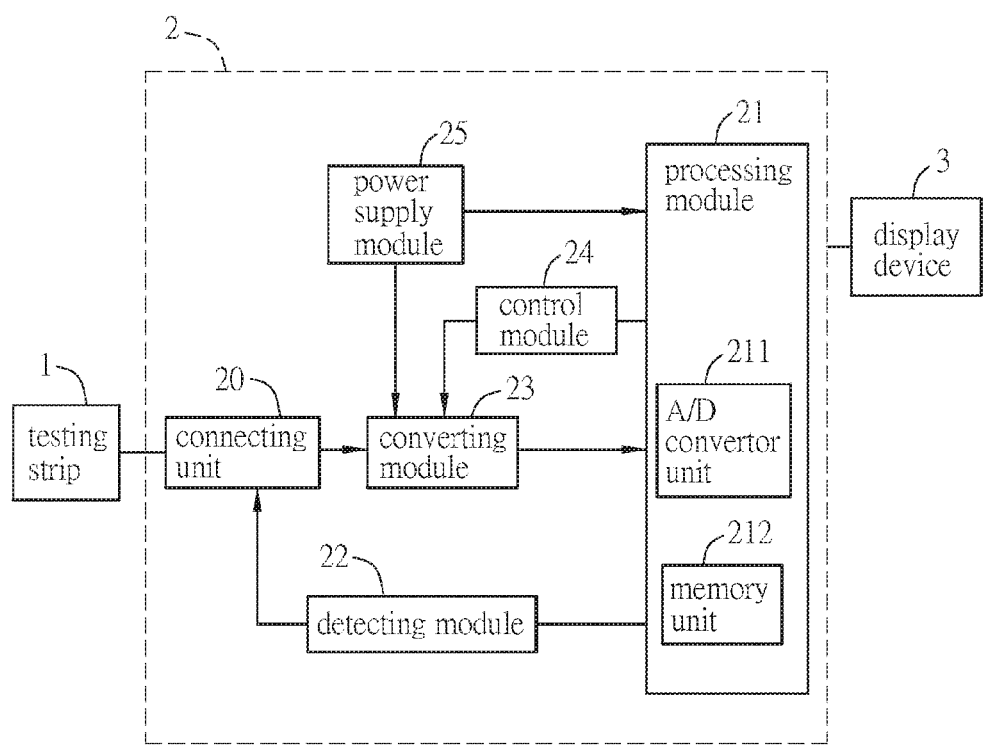
FIG. 1C is a block diagram showing a measuring device applied with the testing strip of FIG. 1B.

FIG. 1C is a block diagram showing a measuring device applied with the testing strip of FIG. 1B. With reference to FIG. 1B and FIG. 1C, the testing strip 1 is electrically connected to a measuring device 2. In detail, the testing strip 1 is disposed in a connecting unit 20 of the measuring device 2. The connecting unit 20 includes a tank or chamber able to accommodating the testing strip 1. Thus, the size and the shape of the connecting unit 20 can be designed based on the testing strip 1, and are not for limitation.

In one embodiment, the measuring device 2 further includes a processing module 21, a detecting module 22, a converting module 23, a control module 24, and a power supply module 25. The connections and compositions of the components of the measuring device 2 are not limited and they can be modified based on the desired detection effects and requirements. In this embodiment, the testing strip 1 is electrically connected to connecting unit 20 of the measuring device 2 through the working electrode 14. The detecting module 22 detects whether the testing strip 1 is properly inserted into the connecting unit 20 or not, and reports to the processing module 21 accordingly. The processing module 21 commands the control module 24 to generate voltages within a preset range and provide to the converting module 23 for applying the desired voltages to the blood sample on the testing strip 1. In addition, voltages applied from the measuring device 2 and the power for driving components of the measuring device 2 are all supplied by the power supply module 25.

The memory unit 212 of the processing module 21 stores a plurality of linear correlation data which applied to the processing module 21 to calculate the hematocrit value tested from the blood sample and the calibrated blood glucose value. Finally, a display device 3 shows the calibrated blood glucose value accordingly.

Figure 1D:
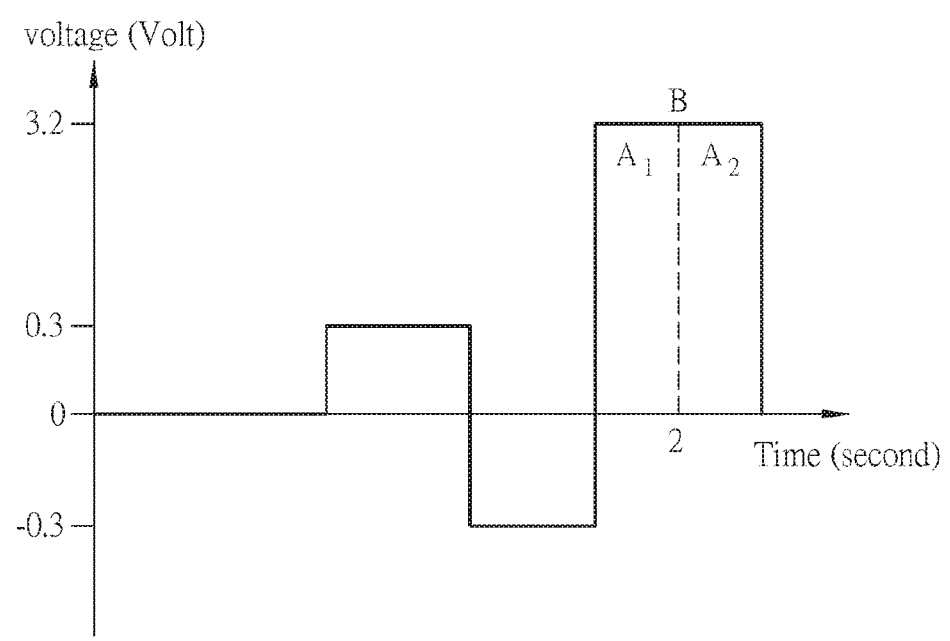
FIG. 1D is a schematic diagram showing the applied voltages in accordance with the detection method of FIG. 1A.

The actual operation and application of the detection method of the invention along with the above mentioned components (the testing strip 1 and the measuring device 2) will be described in more detail herein below. FIG. 1D is a schematic diagram showing the applied voltages in accordance with the detection method of FIG. 1A. With reference to FIGS. 1A and 1D, after injecting the blood sample into the reaction portion 131 of the testing strip 1 and inserting the testing strip 1 into the measuring device 2, the detecting module 22 feedbacks to the processing module 21. Then, the processing module 21 commands the control module 24 to start applying the preset voltages to the testing strip 1. In the step S11, the control module 24 controls the converting module 23 to apply a first voltage between the working electrode 14 and the auxiliary electrode 15 for generating a first current. The current value of the generated first current is measured by the measuring device 2. At the same time, the current value of the first current is converted by the converting module 23 so as to form a first voltage curve. When the values of the first electrode curve is sent back to the processing module 21, the analog to digital (A/D) convertor unit 211 processes the first voltage curve according to the linear correlation data stored in the memory unit 212 so as to obtain or transform the first blood glucose value of the blood sample.

The first blood glucose value obtained by the step S11 is referred to the original blood glucose value of the blood sample. However, some factors existed in the blood sample, such as the interferences other than the detected target that can affect the electrochemical reaction and measured result, can cause the error of the detected first blood glucose value. Accordingly, it is necessary to filter the interference factors out for obtaining a more accurate blood glucose concentration value. In addition, the first blood glucose value is not calibrated by the hematocrit index yet.

Then, the step S13 is performed to apply a second voltage to the blood sample for obtaining a second blood glucose value of the blood sample. In the step S13, which is substantially similar to the above mentioned step S11, the processing module 21 commands the control module 24 to start applying a preset voltage to the testing strip 1. In more detailed, the control module 24 controls the converting module 23 to apply a second voltage between the working electrode 14 and the auxiliary electrode 15 for generating a second current. The current value of the generated second current is measured. At the same time, the current value of the second current is converted by the converting module 23 so as to form a second voltage curve. When the values of the second electrode curve is sent back to the processing module 21, the analog to digital convertor unit 211 processes the second voltage curve according to the linear correlation data stored in the memory unit 212 so as to obtain or transform the second blood glucose value of the blood sample.

The first voltage applied to the blood sample is ranged from 0 to 1 volts. For example, the first voltage can be 0.3 volts and lasted for 2 seconds. Afterwards, the second voltage applied to the blood sample is ranged from −1 to 0 volts, preferably from −0.9 to −0.1 volts, and is optimum −0.3 volt. The ranges and preferred ranges of the first and second voltages can be the range defined by any two real numbers within the above ranges. The first and second voltages are applied for 0.5 to 5 seconds, and preferably for 2 seconds.

In the two-stage voltages applying, the step S11 can conduct an oxidation reaction of the blood sample, and the step S13 can conduct a reduction reaction of the blood sample. This process can effectively reduce the interferences existed in the blood sample, thereby removing the error of the detected blood glucose value caused by the interferences. In this embodiment, although the steps S11 and S13 can obtain different blood glucose values, the second blood glucose value obtained by the step S13 is closer to the accrual value than the first blood glucose value obtained by the step S11.

However, the second blood glucose value obtained by the step S13 is still not calibrated by the hematocrit index, which is referred to the ratio (%) of red blood cells contained in the specific amount of blood. The blood glucose (concentration) values may vary with the hematocrit. To most human beings, the standard hematocrit is about 42%. When the hematocrit is higher than 42%, the blood glucose value obtained may be lower than the standard blood glucose; on the contrary, when the hematocrit is lower than 42%, the blood glucose value obtained may be higher than the standard blood glucose. Hence, in order to obtain the more accurate blood glucose value, the pre-measuring of the hematocrit is needed. Then, the compensation of the blood glucose according to hematocrit is processed so as to obtain a more accurate blood glucose value.

As mentioned above, most techniques recently are not able to obtain accurate hematocrit, or even need to obtain the blood glucose and the hematocrit through more complicated steps and calibrations. This is not only wasting human power and processing time, but also getting limiting effects. However, in the present invention, the step S15 is applying a third voltage to the blood sample to get a hematocrit index of the blood sample.

In the step S15, the processing module 21 indicates the control module 24 to apply a third voltage between the working electrode 14 and the auxiliary electrode 15, and generating a third current there between. The third current is also measured. At the same time, the third current is converted by the converting module 23 so as to form a third voltage curve. When the third voltage curve is delivered back to the processing module 21, the analog to digital convertor unit 211 processes the third voltage curve according to the data stored in the memory unit 212, thereby obtaining the hematocrit index corresponding to the blood sample based on the third voltage curve. Referring to FIG. 1D, the hematocrit index can be calculated according to the following equation:

$$\text{The hematocrit index} = (A1/A2) \times 100.$$

In this embodiment, the third voltage applied for obtaining the hematocrit index is between 1 and 4 volts, and is preferably 3.2 volts. The third voltage is applied for from 0.5 to 5 seconds, and preferably 2 seconds. In this embodiment, the third voltage is applied for 2 seconds. In this step, a first median A1 of current values (the third current), as the third voltage is applied from 0 to 0.5 seconds, is obtained, and a second median A2 of the current values (the third current), as the third voltage is applied from 1 to 2 seconds, is also obtained. In more detailed, the current values of the third current are sampled periodically (e.g. the sampling interval is 0.005 seconds). Accordingly, if the third voltage is applied from 0 to 0.5 seconds, totally 100 current values can be retrieved ((0.5-0) seconds/0.005 seconds=100). Then, the 100 current values are sorted in order, and the median of the sorted current values (the number 50th current value from the total 100 current values) is obtained as the first median A1. The second median A2 can be obtained by a similar method, so the detailed description thereof will be omitted.

To be noted, the calculation method for obtaining the first and second medians A1, A2 here can be fit to any case such as the third voltage is applied for a longer time. For example, when the third voltage is applied for 3 seconds, this step is also to obtain the same first median A1 of the current values as the third voltage is applied from 0 to 0.5 seconds, and to obtain the second median A2 of the current values as the third voltage is applied from 1 to 2 seconds. In other words, the sampling procedures for calculating the first and second medians are the same.

In the detection method of the invention, the second voltage and the third voltage are reversed voltages, and the first voltage and the second voltage are also reversed voltages. That is, the first voltage and the third voltage are voltages with the same polarity. In practice, the absolute value of the third voltage is larger than that of the first voltage.

After obtaining the hematocrit index by performing the step S15, the step S17 is performed to transform the hematocrit index into a hematocrit value and calibrate the second blood glucose value according to the hematocrit value. In other words, the method can compensate the target concentration according to the obtained hematocrit index. The calibration procedure will be described in the following example.

As mentioned above, the step S13 is to apply a second voltage and then the step S15 is to apply a third voltage. These steps S13 and S15 can remove the effect of the glucose concentration in the blood sample, so the hematocrit index obtained in the step S15 is more accurate. Accordingly, the method of this embodiment can calculate the hematocrit value based on the more accurate hematocrit index obtained by the step S15. Then, the obtained more accurate hematocrit value is further used to calibrate the relative accurate second blood glucose value obtained by the step S13, thereby improving the accurate of the measuring result.

To be noted, the above-mentioned first, second, and third voltages are all direct voltages. Compared with the conventional approach, which needs to apply the direct voltage and alternative voltage in turn, the invention has the advantage of simplifying the detection process and apparatus thereof.

When applying the third voltage, the step S15 can also obtain a hemoglobin index (Hg index) of the blood sample. In more detailed, the step S15 is to calculate the hemoglobin index corresponding to the blood sample according to the third voltage curve as the third voltage is applied. As shown in FIG. 1D, the hemoglobin index can be calculated based on the following equation:

$$\text{The hemoglobin index} = \ln[(A1/A2) \times (B/A2) \times 1000].$$

In this embodiment, the third voltage is applied for 2 seconds, and the calculating method for obtaining the hemoglobin index will be described hereinafter. In this case, this step S15 is to obtain the first median A1 of the current values (the third current) as the third voltage is applied from 0 to 0.5 seconds, to obtain the second median A2 of the current values (the third current) as the third voltage is applied from 1 to 2 seconds, and to obtain the third median B of the current values (the third current) as the third voltage is applied from 0 to 2 seconds. The calculating method for obtaining the first, second and third medians A1, A2, and B can be referred to the method for obtaining the hematocrit index, so the detailed description thereof will be omitted.

After obtaining the hemoglobin index by performing the step S15, the steps S17 and S19 are performed simultaneously. The details of the step S17 have been described in the above, so they are not described again. The step S19 is to transform the hemoglobin index into the blood hemoglobin value. In other words, the detection method of the invention can compensate the target concentration according to the hematocrit index. The calibration procedure will be described in the following example.

To be noted, the performing order of the steps S17 and S19 is not a limitation of the invention. In this invention, the hematocrit index and hemoglobin index of the blood sample can be both obtained by applying the third voltage (step S15), and the calibrated blood glucose value and the blood hemoglobin value can be obtained by the steps S17 and S19, respectively. In other words, the detection method of the invention can simultaneously retrieve accurate blood glucose value and blood hemoglobin value by a single and dual-functional testing strip 1 in cooperated with a single measuring device 2 within a single testing procedure.

Figure 2:
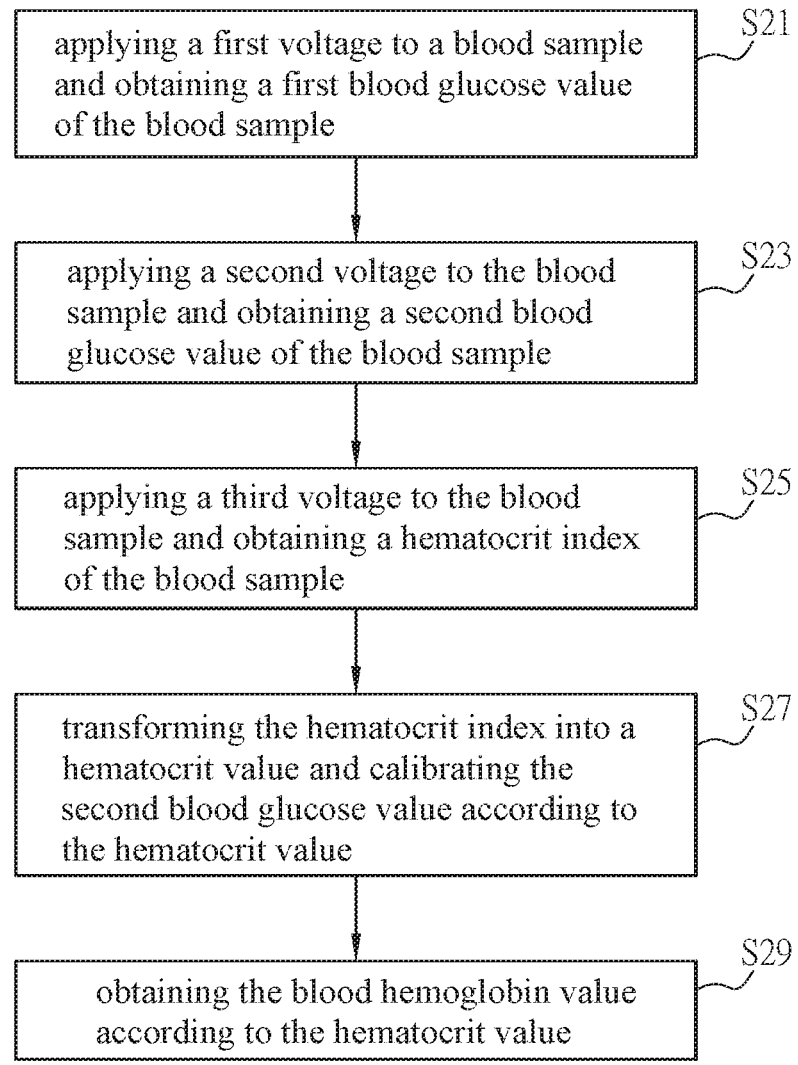
FIG. 2 is a flow chart of a detection method according to another preferred embodiment of the invention.

FIG. 2 is a flow chart of a detection method according to another preferred embodiment of the invention. Referring to FIG. 2, the detection method of this embodiment includes at least the following steps of: applying a first voltage to a blood sample and obtaining a first blood glucose value of the blood sample (step S21); applying a second voltage to the blood sample and obtaining a second blood glucose value of the blood sample (step S23); applying a third voltage to the blood sample and obtaining a hematocrit index of the blood sample (step S25); transforming the hematocrit index into a hematocrit value and calibrating the second blood glucose value according to the hematocrit value (step S27); and obtaining the blood hemoglobin value according to the hematocrit value (step S29). The steps S21, S23, S25 and S27 can be referred to the above-mentioned steps S11, S13, S15 and S17, so the detailed description thereof will be omitted. Only the step S29 and a part that is not disclosed in above embodiment will be discussed in the following example.

With utilizing the testing strip 1 and the measuring device 2 as described in the previous embodiment, the detection method in this embodiment is to obtain the blood hemoglobin value according to the obtained hematocrit index. In more detailed, the step S27 is to transform the hematocrit index (obtained by the step S25) into a hematocrit value and then to obtain the blood hemoglobin value corresponding to the blood sample according to the following equation:

blood hemoglobin value=hematocrit value×0.3453+ 0.0097.

The following and accompanying figures take an experiment for an example to describe the main details of the detection method of the invention and the practical applying method and the effect of the implantation of the composition in accordance with the embodiments of the present invention. It will show that the detection method of the invention can precisely compensate the blood glucose error and detect both of the blood glucose value and the blood hemoglobin value simultaneously.

The obtaining method of blood sample of the present invention includes: collecting the venous blood with the blood collection tube (Heparin Green) and rolling for 30 minutes for well-mixing with oxygen on the roller.

Experiment 1: Obtaining the Linear Correlation of Hematocrit Index to Hematocrit Value Referring to the following Table 1, the testing samples are prepared with three blood samples with different blood glucose concentrations (group I: 30-50 mg/dL, group II: 120-200 mg/dL, and group III: 300-500 mg/dL) and five blood samples with different hematocrit values (they are 10±1%, 25±1%, 42±1%, 60±1% and 70±1%, respectively).

TABLE 1

| hematocrit value testing | Group I 30-50 mg/dL | Group II 120-200 mg/dL | Group III 300-500 mg/dL |
|---|---|---|---|
| 10 ± 1% | T1 | T6 | T11 |
| 25 ± 1% | T2 | T7 | T12 |
| 42 ± 1% | T3 | T8 | T13 |
| 60 ± 1% | T4 | T9 | T14 |
| 70 ± 1% | T5 | T10 | T15 |

The obtained testing samples T1-T15 are detected by the detection method of the invention (using YSI blood glucose meter). In practice, the DELBio™ testing strip is used to detect the testing samples under 23±2° C. In more detailed, a first voltage is applied to the testing sample to obtain a first blood glucose value, and then a second voltage is applied to the testing sample to obtain a second blood glucose value. Next, a third voltage is applied to the testing sample to obtain a hematocrit index. The test results are shown in FIG. 3.

Figure 3:
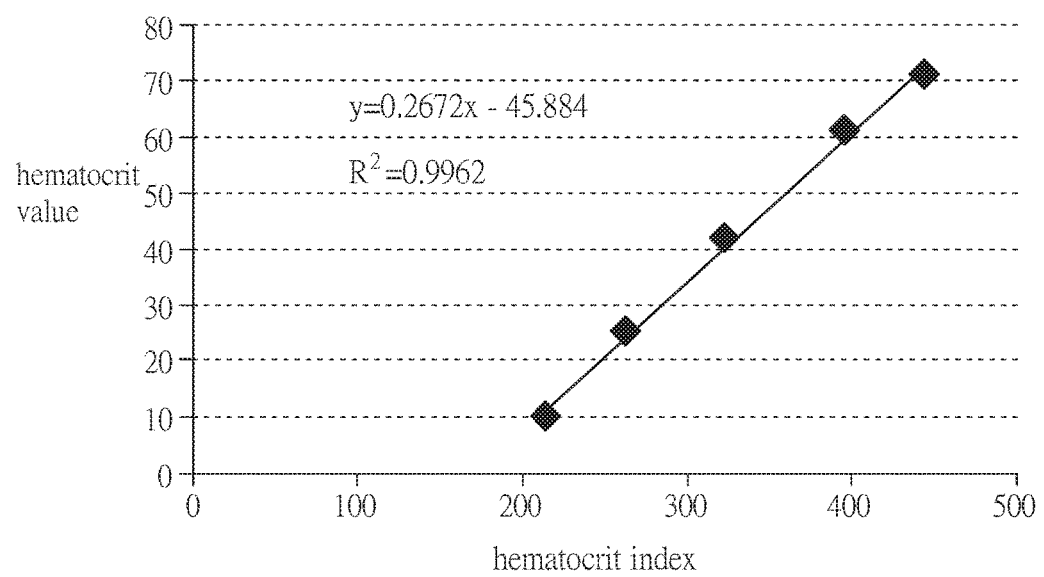
FIG. 3 is a schematic diagram showing a linear relationship between the hematocrit index and the hematocrit value obtained in the detection method of FIG. 1A.

FIG. 3 shows that the hematocrit index and the hematocrit value have a substantially linear relationship, wherein $R^2$ is greater than 0.9 as the hematocrit value is ranged between 0-70%.

In summary, the detection method of the invention is applied to detect the blood glucose value and hemoglobin value of a blood sample. In the detection procedure, the blood sample is injected into an electrochemical testing strip, which is configured with a working electrode and an auxiliary electrode for conducting the electrochemical reaction of the blood sample. The present invention obtains a sensing current corresponding to the original blood glucose value, a sensing current for an optimum blood glucose value with removing the effect of interferences, and a hematocrit index (HCT index) and a hemoglobin index corresponding to the blood sample, respectively, by applying three-stage voltages in the specific range to the blood sample, and further calibrates the original blood glucose value according to the hematocrit index. Moreover, the present invention also obtained transforms the hemoglobin index to further obtain a blood hemoglobin value. In another embodiment of the invention, the present invention can also obtain the hematocrit value and the blood hemoglobin value according to the hematocrit index.

Compared with the conventional techniques, the detection method of the invention is to apply a first voltage and a second voltage to the blood sample for obtaining a first blood glucose value and a second blood glucose value, respectively. Since the second voltage is a reversed voltage with respect to the first voltage, it can effectively remove the effect of the interferences in the blood sample to the detected blood glucose value. Besides, the detection method is further to apply a third voltage, after applying the second voltage, to obtain a hematocrit index and a hemoglobin index of the blood sample. The obtained indexes can be processed to calibrate the blood glucose value and generate the blood hemoglobin value. In other words, the detection method of the invention can simultaneously retrieve accurate blood glucose value and blood hemoglobin value by a single and dual-functional strip in cooperated with a single measuring device within a single testing procedure. This feature can sufficiently reduce the detection time and simplify the detection processes and apparatus thereof.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A detection method for detecting a blood glucose value and a blood hemoglobin value of a blood sample, comprising steps of:
    applying a first voltage to the blood sample and obtaining a first blood glucose value;
    applying a second voltage to the blood sample and obtaining a second blood glucose value;
    applying a third voltage to the blood sample and obtaining a hematocrit index and a hemoglobin index;
    transforming the hematocrit index into a hematocrit value and calibrating the second blood glucose value according to the hematocrit value; and
    transforming the hemoglobin index into a hemoglobin value.

2. The detection method according to claim 1, wherein the third voltage is between 1 and 4 volts.

3. The detection method according to claim 1, wherein the third voltage is applied for 2 seconds.

4. The detection method according to claim 3, wherein the step of obtaining the hematocrit index comprises:
    obtaining a first median A1 of current values as the third voltage is applied from 0 to 0.5 seconds; and
    obtaining a second median A2 of current values as the third voltage is applied from 1 to 2 seconds;
    wherein, the hematocrit index is $(A1/A2) \times 100$.

5. The detection method according to claim 4, wherein the step of obtaining the hemoglobin index comprises:
    obtaining a third median B of current values as the third voltage is applied from 0 to 2 seconds;
    wherein, the hemoglobin index is $\ln[(A1/A2) \times (B/A2) \times 1000]$.

6. The detection method according to claim 1, wherein the first voltage, the second voltage and the third voltage are direct voltages.

7. The detection method according to claim 1, wherein the step of transforming the hematocrit index into the hematocrit value is performed based on a linear correlation formula.

8. A detection method for detecting a blood glucose value and a blood hemoglobin value of a blood sample, comprising steps of:
    applying a first voltage to the blood sample and obtaining a first blood glucose value;
    applying a second voltage to the blood sample and obtaining a second blood glucose value;
    applying a third voltage to the blood sample and obtaining a hematocrit index;
    transforming the hematocrit index into a hematocrit value and calibrating the second blood glucose value according to the hematocrit value; and
    obtaining a hemoglobin value according to the hematocrit value.

9. The detection method according to claim 8, wherein the third voltage is between 1 and 4 volts.

10. The detection method according to claim 8, wherein the third voltage is applied for 2 seconds.

11. The detection method according to claim 10, wherein the step of obtaining the hematocrit index comprises:
    obtaining a first median A1 of current values as the third voltage is applied from 0 to 0.5 seconds; and
    obtaining a second median A2 of current values as the third voltage is applied from 1 to 2 seconds;
    wherein, the hematocrit index is $(A1/A2) \times 100$.

12. The detection method according to claim 8, wherein the first voltage, the second voltage and the third voltage are direct voltages.

13. The detection method according to claim 8, wherein the step of transforming the hematocrit index into the hematocrit value is performed based on a linear correlation formula.

* * * * *